(12) United States Patent
Polettini et al.

(10) Patent No.: US 8,500,712 B2
(45) Date of Patent: Aug. 6, 2013

(54) KIT FOR COLLECTING BLOOD, PREFERABLY PERIPHERAL BLOOD, FOR THE PRODUCTION OF STEM CELLS

(75) Inventors: Marco Polettini, Sutri (IT); Alessandra Gambacurta, Rome (IT)

(73) Assignee: Thankstem Srl, Udine (IT)

( * ) Notice: Subject to any disclaimer, the term of this patent is extended or adjusted under 35 U.S.C. 154(b) by 355 days.

(21) Appl. No.: 12/922,498

(22) PCT Filed: Mar. 17, 2009

(86) PCT No.: PCT/EP2009/053144
§ 371 (c)(1),
(2), (4) Date: Sep. 14, 2010

(87) PCT Pub. No.: WO2009/115522
PCT Pub. Date: Sep. 24, 2009

(65) Prior Publication Data
US 2011/0017733 A1    Jan. 27, 2011

(30) Foreign Application Priority Data
Mar. 18, 2008    (IT) .............................. UD2008A0058

(51) Int. Cl.
*A61B 19/00*    (2006.01)
*C12N 5/00*    (2006.01)
(52) U.S. Cl.
USPC ........................................ 604/403; 435/325
(58) Field of Classification Search
USPC ............... 604/6.02, 6.07, 317, 403; 210/645, 210/646; 435/455, 472, 435
See application file for complete search history.

(56) References Cited

U.S. PATENT DOCUMENTS

| 6,033,907 A | 3/2000 | Williams |
| 2004/0101962 A1 | 5/2004 | Kremer et al. |
| 2005/0214935 A1 | 9/2005 | Kuwabara et al. |
| 2006/0020227 A1 | 1/2006 | Moore et al. |
| 2006/0060494 A1 | 3/2006 | Goodman et al. |
| 2007/0202189 A1* | 8/2007 | Ahlfors .......................... 424/548 |
| 2008/0038238 A1 | 2/2008 | Huberman et al. |

FOREIGN PATENT DOCUMENTS

| EP | 1 767 935 A1 | 3/2007 |
| JP | 09-248288 A | 9/1997 |
| JP | 2003-009851 A | 1/2003 |
| JP | 2005-168494 A | 6/2005 |
| JP | 2006-512060 A | 4/2006 |
| JP | 2006-204232 A | 8/2006 |
| WO | 03/083092 A1 | 10/2003 |
| WO | 2004/043990 A2 | 5/2004 |
| WO | 2005001019 A1 | 1/2005 |
| WO | 2005/046570 A2 | 5/2005 |
| WO | 2007112084 A2 | 10/2007 |
| WO | 2007/131200 A2 | 11/2007 |
| WO | 2008023874 A1 | 2/2008 |
| WO | 2008/034740 A1 | 3/2008 |

OTHER PUBLICATIONS

Data Sheet for M-CSF, http://datasheets.scbt.com/sc-1326.pdf.*
Int'l Search Report issued on Jul. 15, 2009 in Int'l Application No. PCT/EP2009/053144.
Written Opinion issued on Jul. 15, 2009 in Int'l Application No. PCT/EP2009/053144.
Cen-Med Website, "http://www.bloodtubes.com/products.htm", Greiner Vacuette Coagulation tubes, pp. 1-4, Aug. 18, 2008.
AJ Wagers et al., "Cell fate determination from stem cells", Gene Therapy, vol. 9 pp. 606-612, (2002).
Linda C. Griffith et al., "Tissue Engineering—Current Challenges and Expanding Opportunities", www.sciencemag.org, vol. 295, pp. 1009-1014, Feb. 8, 2002.
Masataka Kuwana et al., "Human circulating CD14+ monocytes as a source of progenitors that exhibit mesenchymal cell differentiation", Journal of Leukocyte Biology, vol. 74, pp. 833-845, Nov. 2003.
Maud Condomines et al., "Functional Regulatory T Cells Are Collected in Stem Cell Autografts by Mobilization with High-Dose Cyclophosphamide and Granulocyte Colony-Stimulating Factor1", Journal of Immunology, vol. 176, pp. 6631-6639, (2006).
Yong Zhao et al., "A human peripheral blood monocyte-derived subset acts as pluripotent stem cells", PNAS, vol. 100, No. 5, pp. 2426-2431, Mar. 3, 2003.
Won Jun Kang, et al, "Tissue Distribution of 18F-FDG-Labeled Peripheral Hematopoietic Stem Cells After Intracoronary Administration in Patients with Myocardial Infarction", The Journal of nuclear Medicine, vol. 47, No. 8, pp. 1295-1301, Aug. 2006.
M. Rabinovitch et al., "Call Shape Changes Induced by Cationic Anesthetics", The Journal of Experimental medicine, vol. 143, pp. 290-304, (1976).
Mai Hou et al., "Transplantation of mesenchymal stem cells from human bone marrow improves damaged heart function in rats", International Journal of Cardiology, vol. 115, pp. 220-228, (2007).
Joerg Fiedler et al., "IGF-I and IGF-II stimulate directed cell migration of bone marrow-derived human mesenchymal progenitor cells", Biochemical and biophysical Research Communications, vol. 345, pp. 1177-1183, (2006). Rajiv Gulati et al., "Diverse Origin and Function of cells with Endothelial Phenotype Obtained from Adult Human Blood", Circulation Research: Journal of the American heart Association, vol. 93, pp. 1023-1025, (2003).
Zhang et al., "Preliminary research on preparation of porcine bladder acellular matrix graft for tissue engineering applications", vol. 85, No. 38, pp. 2724-2727, Oct. 12, 2005 (English translation of abstract only).
Koerbling et al., "Hepatocytes and Epithelial Cells of Donor Origin in Recepients of peripheral-Blood Stem Cells", The New England Journal of Medicine, vol. 346, No. 10, pp. 738-746, Mar. 7, 2002.
Okazaki et al., "Macrophage Colony-Stimulating Factor Induces Vascular Endothelial Growth Factor production in Skeletal Muscle and Promotes Tumor Angiogenesis", The Journal of Immunology, vol. 174, pp. 7531-7538, (2005).
Office Action issued Jan. 8, 2013 in JP Application No. 2011-500197.

* cited by examiner

*Primary Examiner* — Melanie Hand
(74) *Attorney, Agent, or Firm* — Panitch Schwarze Belisario & Nadel LLP

(57) ABSTRACT

A kit for collecting blood, preferably peripheral blood, for the production of pluripotent stem cells comprises at least a first container, able to contain the blood taken, which contains an anticoagulant and the substance MCSF (Macrophage Colony Stimulating Factor).

9 Claims, 1 Drawing Sheet

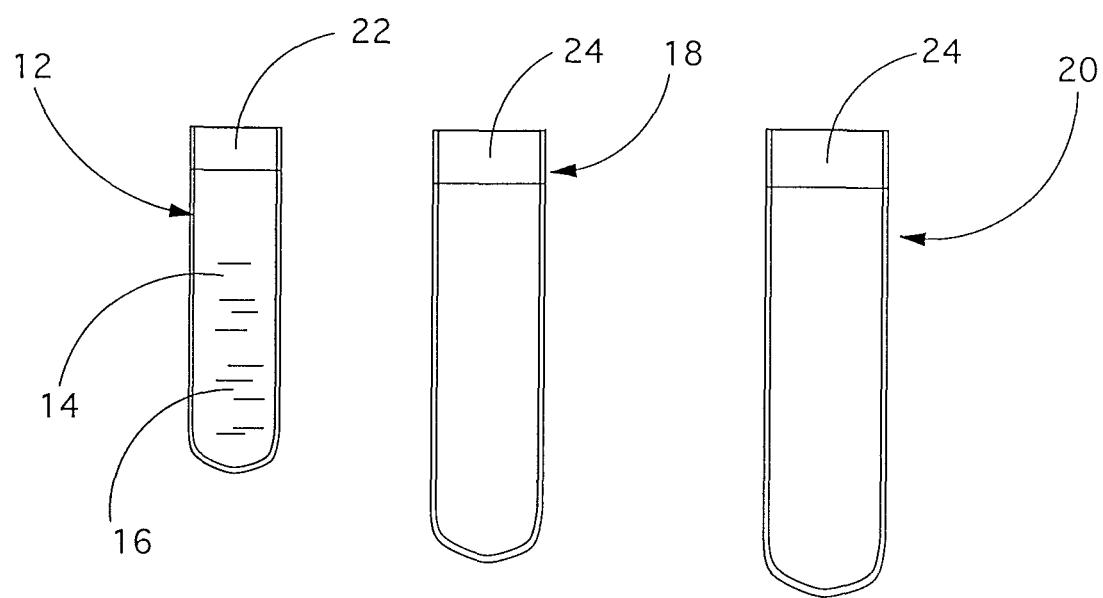

KIT FOR COLLECTING BLOOD, PREFERABLY PERIPHERAL BLOOD, FOR THE PRODUCTION OF STEM CELLS

CROSS-REFERENCE TO RELATED APPLICATION

This application is a section 371 of International Application No. PCT/EP2009/053144, filed Mar. 17, 2009, which was published in the English language on Sept. 24, 2009 under International Publication No. WO 2009/115522 A1 and the disclosure of which is incorporated herein by reference.

FIELD OF THE INVENTION

The present invention concerns a kit for collecting blood, preferably of the peripheral type, for the production of adult stem cells.

BACKGROUND OF THE INVENTION

In recent years the use of stem cells in therapy has had widespread approval due to the successes obtained in the treatment of pathologies which until now were considered incurable.

However, the known methods for obtaining stem cells are long, laborious and expensive.

Pluripotent stem cells (PSC) are a source available not only for research but also for the creation of drugs and for transplants (Wagers A. J. et al., 2002; Griffith L. G. et al., 2002).

There are embryo and adult stem cells: the former derive from 8-day blastocysts, while the adult ones can be obtained mainly from bone marrow, adipose or muscular tissue, peripheral blood and the umbilical cord.

The definition of stem cell is constantly evolving and, at the moment, there is no general consensus or standard method to isolate them or identify them. For all these cells, embryonic (ES), and adult, both haemopoietic (HSC) and mesenchymal (MSC) (Kuwana M. et al., 2003), various genetic markers have been identified, of which some are common to many cell types (Condomines M. et al., 2006; Kang W. J. et al., 2006; Zhao Y. et al., 2003; Rabinovitch M. et al., 1976).

At the moment, research is more oriented toward the use of stem cells isolated from embryonic tissue, fetuses and the umbilical cord, but this is creating legal and ethical problems.

Above all, as of today the use of these cells has various counter-indications such as: risks of infection, risk of rejection if transplanted and, in some mammals such as horses, the development of teratomas.

To overcome these problems, in "in vivo" therapy it is known to use autologous stem cells, preferably isolated from bone marrow, adipose tissue or peripheral blood. Starting from adult stem cells there is a differentiation step "in vitro" (or "ex vivo") of the stem cells in the cell line desired by means of specific factors of induction of the differentiation, and a subsequent transplant step "in vivo" of the differentiated cell line obtained. In these methods there is the disadvantage of rejection phenomena since the differentiated cells, reintroduced into the organism concerned, are not recognized as self-cells, inasmuch as they lose the self-recognition factors during the step of induced differentiation in vitro.

In man, taking the stem cells from peripheral blood entails their purification through a process called aphaeresis or leucoaphaeresis. The cells are extracted from the blood, collected and then inoculated into patients immediately after chemotherapy or radiotherapy.

In aphaeresis, which lasts from 6 to 8 hours, the blood is taken from the vein of an arm or a vein of the neck or chest, and made to pass through a machine that removes the stem cells. The blood, thus purified, returns to the patient, whereas the cells collected are preserved through refrigeration in liquid nitrogen (Condomines M. et al., 2006; Kang W. J. et al., 2006). This technique, apart from being painful, is also extremely stressful for the patient. Above all, the technique does not provide a real discrimination and/or purification of the stem cells circulating. The main known techniques for purification are:

use of growth factors or plate derivates (TGF-B, VEGF), but the economic costs of extracting these are prohibitive (Hou M. et al, 2006);

isolation of stem cells taken from the bone marrow, which allows to purify and hence use for therapy about 15% of cells contained in the extracted material;

isolation of stem cells from adipose tissue, which requires a prior surgical removal of considerable quantities of tissue from the donor and does not allow intravenous administration;

IGF-1 (insulin-like growth factor 1) known as Tendotrophin (Fiedler J. et al., 2006);

UBM (urinary bladder matrix): this is a derivate of the pig, containing cytokines (but not nucleate cells), which induce cicatrization of the wound but not the regeneration of the zone with the lesion (Zhang Y S et al., 2005).

Another known method is described by Zhao Y. et al., in the article "A human peripheral blood monocyte-derived subset acts as pluripotent stem cells" and in WO-A-2004/043990. This is a method to prepare stem cells deriving from monocytes, which comprises the steps of isolating monocytes from peripheral blood, putting them into contact with a mitogenic component and subsequently effecting the culture of the monocytes from peripheral blood in conditions suitable for the propagation of the cells.

This method, which initially requires a step of isolating the monocyte and then an expansion step in a culture mean, is very long, about 15-20 days, to obtain a significant number of stem cells, and does not allow to obtain pluripotent stem cells, that is, non specialized, suitable to be inoculated directly and after a short time into the patient.

Again in the framework of preparing stem cells from monocytes, the documents WO-A-2005/046570, WO-A-2007/131200 and WO-A-03/083092 are also known. However, since they have to carry out a preliminary purification of the blood in order to isolate only a cell fraction, that is, the monocytes, and a subsequent expansion in order to obtain the desired stem cells, the methods described in these documents take a very long time, again in the order of 15-40 days, in order to obtain an acceptable quantity of stem cells.

In the light of the above, there is an obvious need to perfect an expansion method, or division and purification of adult stem cells from easily accessible sources, particularly the blood, preferably peripheral blood, which also allows to obtain stem cells suitable for pharmacological treatment.

There is also an obvious need to start the production of stem cells from blood, preferably peripheral, in the shortest possible time, so as to be able to intervene promptly on the patient.

Purpose of the present invention is therefore to achieve a kit for the collection of blood, preferably peripheral blood, for the production of pluripotent stem cells, so as to allow a rapid start to the production of pluripotent stem cells.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

A method for the growth and purification in vitro of stem cells from blood, preferably peripheral blood, developed by the present authors and described in the international patent application PCT/EP2007/059531 in the name of the present Applicant, which is incorporated here in its entirety for reference, allows to obtain adult pluripotent stem cells and comprises a first step having two sub steps:

a) a first substep of growing the stem cells of peripheral blood, after the blood has been taken, by means of in-vitro treatment with MCSF (Macrophage Colony Stimulating Factor) in a concentration comprised between 8-15 nM, preferably 10 nM;

b) a second substep of purification, preferably by means of fractioning on a Ficoll gradient.

The first growth substep may have a variable duration according to the conditions in which the in-vitro treatment is carried out; the authors have verified experimentally that a duration of the in-vitro treatment with MCSF comprised between 24 and 96 hours, advantageously between 48 and 72 hours, leads to a stabilization of the growth, with identification of the stem markers CD 90, CD 90/34, CD34 and CD117. This condition is considered the optimum one.

The purification of the second substep is fundamentally intended to destroy the red corpuscles.

The second step, which uses the semi-products obtained in step b), provides:

c) growth of the stem cells of peripheral blood, purified in step b) by means of in-vitro treatment with MCSF in a concentration comprised between 35-55 nM, preferably 50 nM, more preferably 45 nM.

With these concentrations of MCSF, the cells keep the phenotype of adult pluripotent stem cells.

This second step may have a duration varying between 24 and 96 hours, preferably between 48 and 72 hours.

It has been observed that, on the contrary, using MCSF in a concentration greater than 55 nM (for example 70 nM) already after 24 hours the cells do not keep the phenotype of pluripotent stem cells.

In particular, step a) of division and prior growth in suspension with MCSF after the blood has been taken allows to increase the percentage of stem cells. The subsequent step b) allows to obtain adult pluripotent stem cells which, once administered to the patient, are differentiated directly in vivo, without causing phenomena of rejection or infection.

The effectiveness of this production is borne out by the presence of stem markers CD90, CD90/34, CD34 and CD117, and by the fact that the stem cells do not lose the factors of self-recognition following division or expansion. Such stem cells do not give collateral effects such as phenomena of rejection, infection, development of teratomas, once administered in the patient, and are able to be differentiated "in vivo" and to behave as pluripotent stem cells.

The authors have seen that the cells thus grown by division or expanded, once injected locally or intravenously, acquire "in vivo" (and not "in-vitro", as in known methods in the state of the art by means of suitable growth factors and/or chemical stimuli (Gulati R. et al., 2003; Katz R. L. et al., 2002; Okazaki T. et al., 2005)) all the morphological and chemical characteristics of macrophagic, lymphocytic, epithelial, endothelial, neuronal and hepatocyte cells, according to the needs and pathologies of the living organisms treated. The method is less invasive than other methods used until now to collect stem cells, painless (unlike aphaeresis), and economical.

Finally, the possibility of obtaining these cells easily, and then being able to preserve them for a long time, for example refrigerated in liquid nitrogen, makes the cells obtained with the method according to the invention suitable for autologous transplants and for the treatment of many pathologies (lesions of various type, metabolic illnesses, acute and chronic neurological and inflammatory pathologies).

According to one characteristic of the present invention, a kit for collecting blood, preferably peripheral blood, for the production of pluripotent stem cells according to the method described above, comprises a first container able to contain the blood taken, such as a test tube, containing an anticoagulant and the substance MCSF. Typically, the first container is made of glass.

With the present kit it is possible to collect the blood, preferably peripheral blood, to start rapidly the growth and production of stem cells by means of the method described above and therefore make the production thereof more rapid.

The main advantage of the present invention is therefore that it obtains a sufficient quantity of pluripotent stem cells in a very limited time, even in only 48 hours, compared with methods known to the state of the art, by operating directly on whole blood. Therefore, the kit for collecting blood according to the present invention is proposed as a rapid and effective solution for obtaining pluripotent stem cells directly from blood, preferably peripheral blood.

Typically, the concentration of MCSF in the test tube of the kit according to the present invention varies from about 2 to 20 nM, preferably from about 8 to 10 nM.

Usually, heparin or EDTA is used as anticoagulant.

The presence of the anticoagulant is essential to prevent the start of coagulation of the blood, whereas MCSF is responsible for the procedure of growth an expansion of the stem cells.

According to a variant embodiment of the present invention, the kit can comprise one or more containers, apart from the first container, such as a test tube. The latter are preferably made with at least the internal wall of a material, for example plastic material such as polypropylene (PP), treated with infra-red or gamma rays, which prevents the adhesion of the stem cells to the wall and hence their aggregation, which is a condition deemed to be avoided.

Typically, for the latter, it is a second container to contain the stem cells, obtained for intravenous use and a third container, of different size, for local use.

The stem cells which are produced in said containers can be used immediately or they can be preserved, in liquid nitrogen, so that they can be used subsequently, when the need arises.

According to another variant, said containers, both the one used for taking the blood, which contains the anticoagulant and the MCSF, and also those used for preservation, can be identified by a serial number, common, sequential or generated according to a predetermined criterion, in order to facilitate identification inside the lab where the stem cells are prepared and at the moment of shipment.

For a univocal identification it is possible to use bar codes and/or RFID tags, reading or reading/writing, applied to the containers, in cooperation with relative optical or electromagnetic readers.

The first growth substep of the method described above is preferably started immediately after the blood is sampled, so that the blood does not coagulate in the meantime.

By the words "immediately after" we mean the shortest time possible between the blood being taken and its coagulation, so as to prevent the coagulation of the blood and start the expansion of the stem cells in the shortest time possible after the blood has been taken.

In other words, "immediately after" refers to the fact that the growth of the stem cells is started immediately after the blood is taken from the patient, taking into account that, for the present invention, it is essential that said expansion process is started before the blood coagulates.

In fact, the blood just taken from the patient is put into the test tube with the anticoagulant and the MCSF. The anticoagulant blocks the start of coagulation, whereas the simultaneous presence of MCSF allows the rapid start of the expansion process and guarantees to minimize the times for starting treatment on the patient.

This definition also includes the case where the sample of blood, preferably peripheral, is taken from the patient, anticoagulant is added in order to block the coagulation of the blood which is subjected to a preservation process which does not alter its capacity for producing stem cells.

When it is necessary, the blood is taken from the place where it is stored and is subjected to the expansion process for stem cells as described above, that is, adding the MCSF, obtaining very rapidly the necessary quantity of stem cells.

A procedure to sample and preserve blood, preferably peripheral, therefore comes within the field of the present invention, said procedure being able to produce stem cells in suitable blood banks and its subsequent use, when necessary, for the production of pluripotent stem cells, by adding MCSF.

Typically, after taking the blood from where it is stored, it is put in a test tube which already contains the MCSF in a concentration of 2 to 20 nM, preferably from 8 to 10 nM.

This allows to avoid the complex and expensive procedure of preserving stem cells, which provides for example to use liquid nitrogen as mentioned above, and instead use only the conventional techniques of preserving blood.

DETAILED DESCRIPTION OF A PREFERENTIAL FORM OF EMBODIMENT

With reference to the attached FIG. 1, a kit 10 for collecting peripheral blood according to the present invention, for the production of pluripotent stem cells, comprises a first test tube 12, made of glass, containing the substance MCSF 14 and in this case heparin 16.

The concentration of MCSF in the test tube 11 goes from about 8 to 10 nM.

The kit comprises another two test tubes 18 and 20, made of plastic material such as polypropylene (PP), treated with infrared or gamma rays.

A second test tube 18 is intended for preserving the cells obtained for intravenous use and a third test tube 20 for local use.

It is important that the test tubes 12, 18 and 20 ensure the sterility of their content.

All the test tubes 12, 18 and 20 are provided with a respective stopper 22, 24 to close them.

The stoppers 22, 24 can be pressure, screw or other.

The stopper 22 of the container 12 can be for example of the pressure type.

The stopper 24 of each of the test tubes 18 and 20 can be for example of the screw type.

The sizes of the second test tube 18 are: height 115 mm, diameter 17 mm, thickness 0.3 mm, capacity 12 mL, whereas the sizes of the third test tube 20 are: height 110 mm, diameter 30 mm, thickness 0.3 mm, capacity 40 mL.

Following expansion by means of MCSF according to the present invention, the cells isolated from peripheral blood act "in vivo" as pluripotent stem cells (PSC) and are suitable to solve in the course of a few months incurable lesions or pathologies, or curable only slowly with classical methods and/or drugs.

Materials and Methods

Sampling:

Each sample of peripheral blood, about 0.5-7 ml, was taken from horses and dogs from the lower limbs and immediately put in test tubes containing a suitable quantity of heparin and MCSF (10 nM).

Other anticoagulants, such as EDTA, can in any case be used.

At this point, the first substep of in vitro treatment is carried out, where we have the division and prior growth of the stem cells, thanks to MCSF.

Purification:

The samples of blood were diluted 1:5 in PBS (Phosphate Buffer Saline) containing $NH_4Cl$ (200 mM), to cause lysis of the red corpuscles, centrifuged at 10,000 g, washed twice with PBS and centrifuged again at 200 g. The nucleate cells obtained were incubated for 7-12 hours at 37° C., preferably for 10-12 hours, and purified by fractioning on a Ficoll gradient, then isolated and washed three times with RPMI medium 1640 (Life Technologies, Grand Island, N.Y.).

Once purified, the cells were incubated another 24-72 hours in the presence of 50 ng/ml of MCSF 45 nM, to obtain cells with about 95% cells with phenotype CD90 (as determined by means of cytofluorimetric analysis using a FACScan—Becton Dickinson flow photometer), and then expanded to obtain the number of cells necessary for local or centrifuged treatments at 10,000 g and suspended in PBS at a concentration of about $90 \times 10^3$ cells/ml for intravenous treatments.

Immunostaining:

For cytophenotyping the cells were washed in PBS and then fixed on a slide in formaldehyde 4% in PBS for 20 minutes at 20° C.

To identify the intra-cellular proteins, the cells were permeabilized with 0.5% Triton X-100 for 5 minutes at 20° C. and then incubated for 1 hour with the primary antibodies diluted in PBS containing 1% BSA (to block the aspecific antigen sites). After three successive washes, the slides were then incubated for 45 minutes with the secondary antibody conjugate with the most appropriate fluorochrome: FITC or tetramethylrhodamine B isothiocyanate (TRITC), or Cy5.

All the secondary antibodies were developed using a donkey as host, by Jackson ImmunoResearch.

The immunocytochemistries were carried out at a temperature of 4° C. and in a humidity saturated atmosphere. After three washes, the slides were mounted using "gelvatol_PBS".

The fluorescence images were then acquired by means of a fluorescence microscope using as internal standard a direct immunofluorescence against glyceraldehyde 3-phosphate dehydrogenase (polyclonal sheep antibody produced by Cortex Biochem, San Leandro, Calif.).

As negative controls and in order to calibrate the background levels of fluorescence, slides incubated with aspecific antibodies were used, of the same isotype as the samples concerned.

The method just described was used to identify all the markers (CD90, CD90/34, CD34 and CD117) and the markers reported in the following table.

TABLE characterization of the cells treated with MCSF(PSC)
and microphages isolated from peripheral blood.

|  | Intensity of relative fluorescence | |
|---|---|---|
|  | PSC | Macrophages |
| Surface antigens | | |
| MAC-1 | 76 ± 18 | 84 ± 15 |
| CD14 | 126 ± 29 | 157 + 19 |
| CD34 | 77 ± 16 | 15 ± 5 |
| CD45 | 143 ± 26 | 165 ± 38 |
| Production of cytokines | | |
| IL-1 | 82 ± 27 | 83 ± 12 |
| IL-6 | 43 ± 22 | 67 ± 14 |
| IL-10 | 7 ± 8 | 58 ± 7 |
| TNF- | 25 ± 16 | 67 ± 16 |
| Functional indicators | | |
| Phagocytosis | 187 ± 23 | 195 ± 26 |
| Stimulation Lymphocytes, Abs540 | 0.72 ± 0.07 | 0.17 ± 0.02 |
| Cytotoxicity % | 9 ± 4 | 72 ± 6 |

It is clear that modifications and/or additions of parts may be made to the kit for collecting blood, preferably peripheral blood, for the production of stem cells as described heretofore, without departing from the field and scope of the present invention.

It is also clear that, although the present invention has been described with reference to examples, a person of skill in the art shall certainly be able to achieve many other equivalent forms of kit for collecting blood, preferably peripheral blood, for the production of stem cells, having the characteristics as set forth in the claims and hence all coming within the field of protection defined thereby.

The invention claimed is:

1. A kit for collecting blood for the production of pluripotent stem cells, the kit comprising at least a first container able to contain the blood taken, the first container containing an anticoagulant and an MCSF (Macrophage Colony Stimulating Factor), wherein the concentration of the MCSF in the first container is about 2 nM to about 20 nM.

2. The kit of claim 1, wherein the concentration of the MCSF in the first container is about 8 nM to about 10 nM.

3. The kit of claim 1, wherein the anticoagulant is heparin or EDTA.

4. The kit of claim 1, comprising a closing element for the first container.

5. The kit of claim 1, further comprising at least a second container having at least the internal wall made of a material that prevents adhesion of the stem cells.

6. The kit of claim 5, wherein the material is a plastic material treated with infrared and/or gamma rays.

7. The kit of claim 6, wherein the plastic material is polypropylene (PP).

8. The kit of claim 5, comprising a closing element for each of the containers.

9. The kit of claim 1, wherein the blood is peripheral blood.

* * * * *